United States Patent [19]

Caillouette

[11] Patent Number: 5,577,512
[45] Date of Patent: Nov. 26, 1996

[54] PH DETECTION AND MEASUREMENT OF BODY FLUID

[76] Inventor: James C. Caillouette, 685 Oak Knoll Cir., Pasadena, Calif. 91106

[21] Appl. No.: 537,379

[22] Filed: Oct. 27, 1995

Related U.S. Application Data

[63] Continuation-in-part of Ser. No. 376,830, Jan. 23, 1995, which is a continuation-in-part of Ser. No. 295,399, Aug. 25, 1994, Pat. No. 5,425,377.

[51] Int. Cl.⁶ ............................................ A61B 10/00
[52] U.S. Cl. ............................... 128/759; 128/771
[58] Field of Search ............................. 128/749, 759, 128/760, 771; 604/1; 33/511, 512, 755, 758–760

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 3,777,743 | 12/1973 | Binard et al. . |
| 4,457,313 | 7/1984 | Alter ................................. 128/759 |
| 4,784,158 | 11/1988 | Okimoto ........................... 128/759 |
| 4,820,259 | 4/1989 | Stevens . |
| 4,862,899 | 9/1989 | Bucaro . |
| 5,063,930 | 11/1991 | Nucci . |
| 5,147,288 | 9/1992 | Schiavo . |

*Primary Examiner*—Max Hindenburg
*Attorney, Agent, or Firm*—William W. Haefliger

[57] ABSTRACT

In the method of detecting pH of vaginal moisture, the steps that include providing a pH detection structure on a carrier stick; providing a protective porous layer adjacent the pH detection structure; manipulating the stick to obtain pH detection of vaginal moisture; and including allowing vaginal moisture to penetrate the porous layer for contact with the pH detection structure, and visually observing the detection structure.

38 Claims, 3 Drawing Sheets

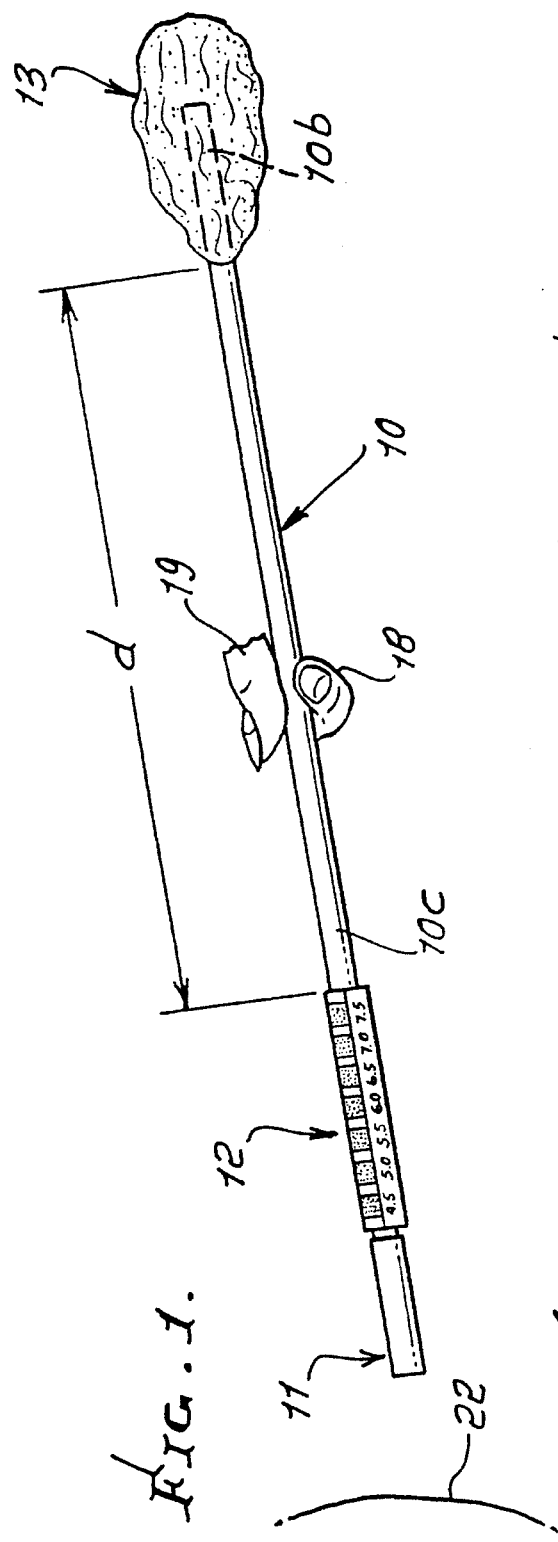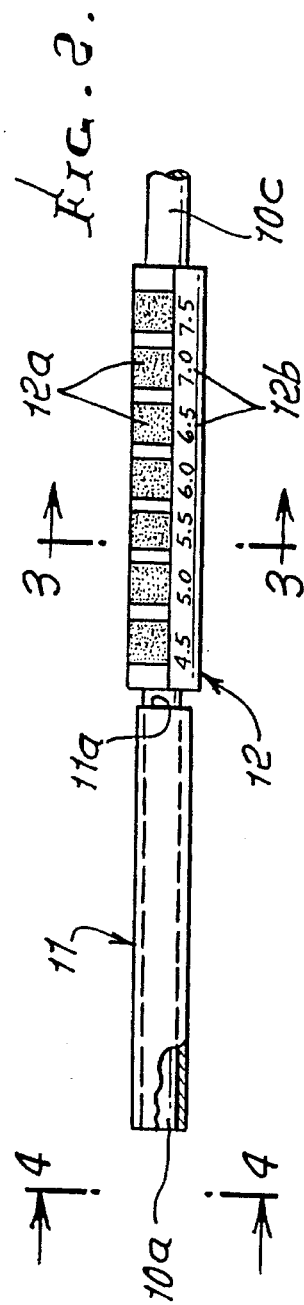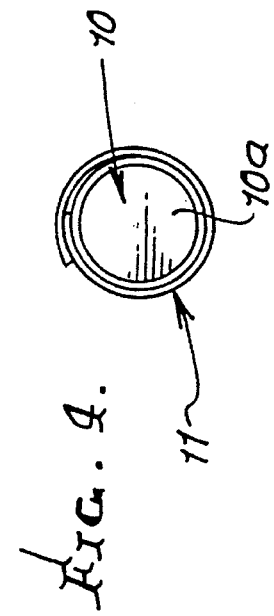

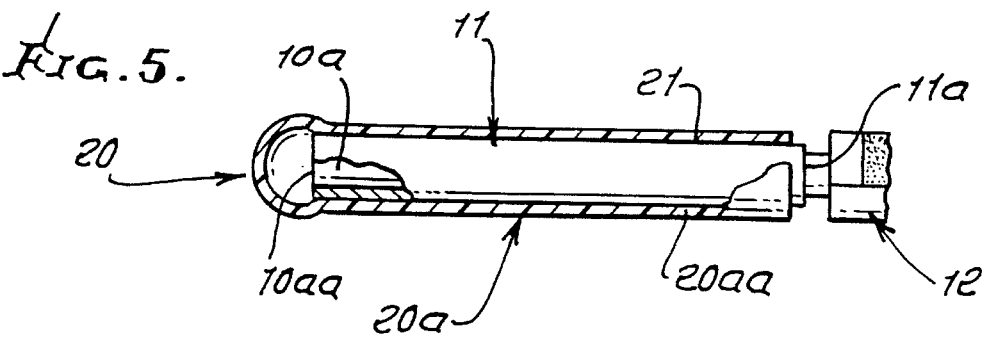
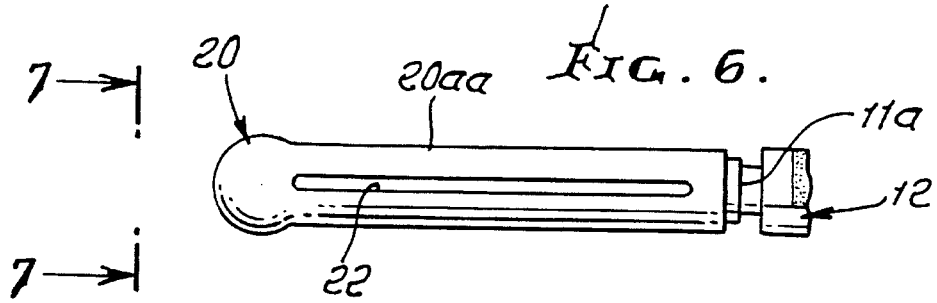
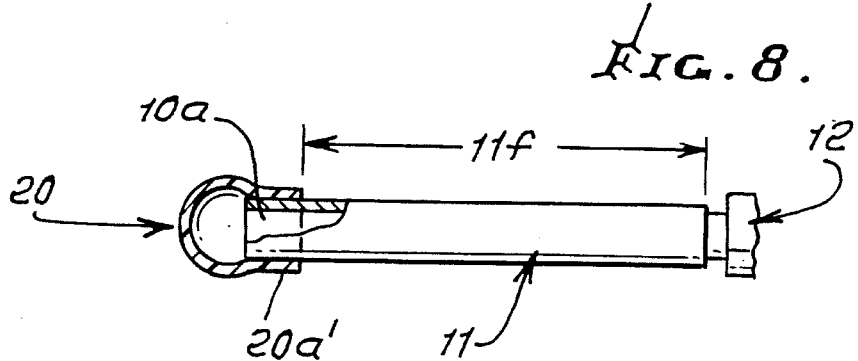
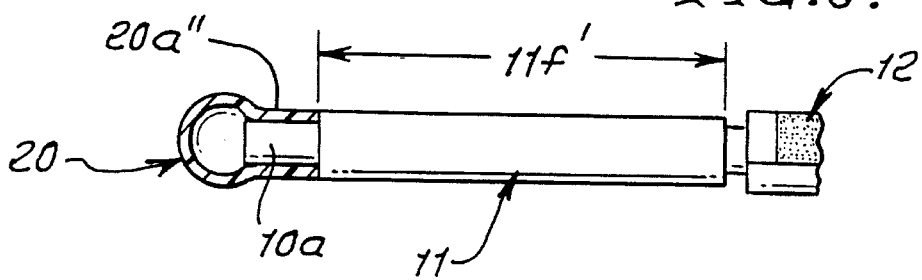

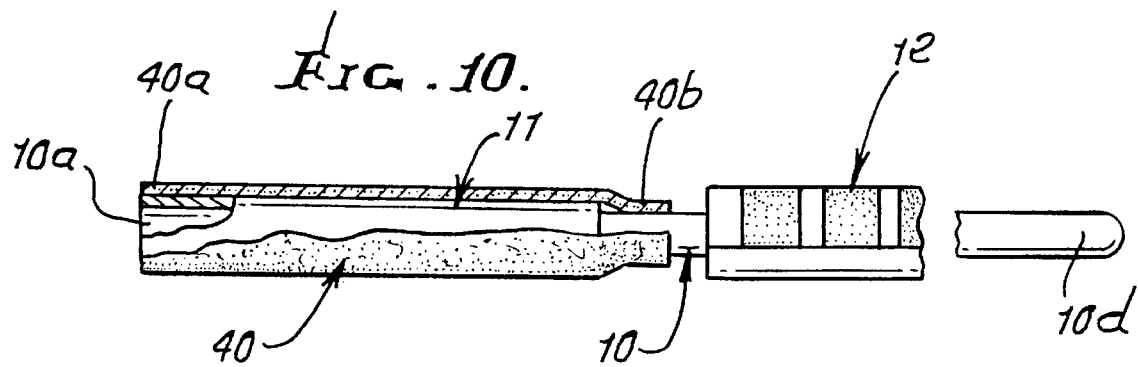
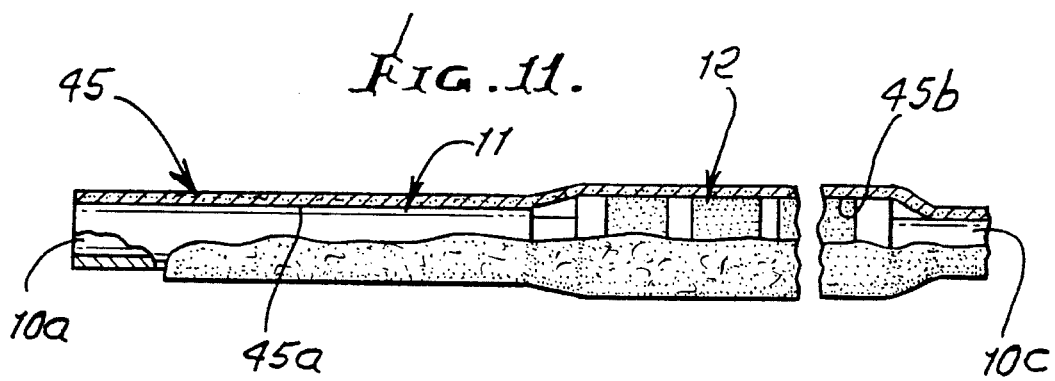
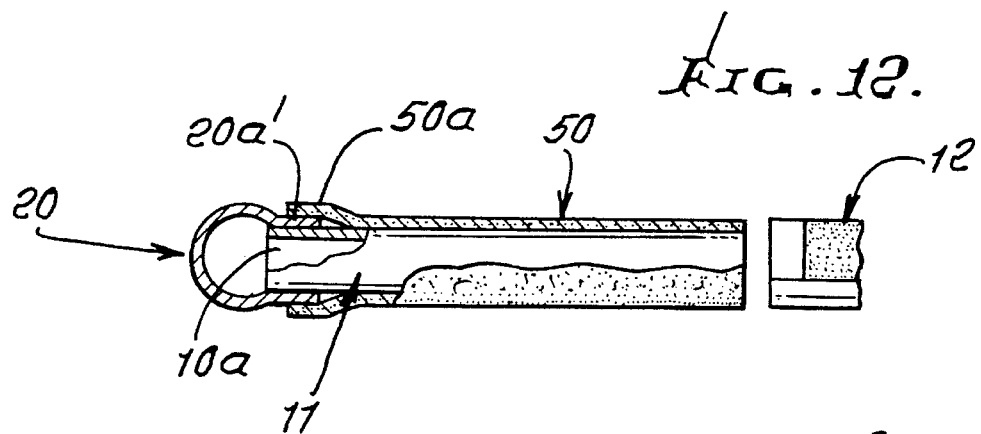
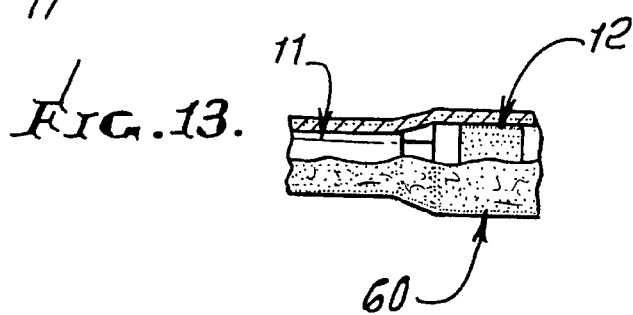

PH DETECTION AND MEASUREMENT OF BODY FLUID

This application is a continuation-in-part of prior U.S. application Ser. No. 08/376,830 filed Jan. 23, 1995, now pending, which is a continuation- in-part of prior U.S. application Ser. No. 08/295,399 filed Aug. 25, 1994, now U.S. Pat. No. 5,425,377

This invention relates generally to pH detection of body fluid, such as vaginal fluid, and more particularly, to a rapid, easily performed method of obtaining pH measurement with protection of vaginal tissue.

BACKGROUND OF THE INVENTION

There is continual need to obtain pH detection, such as measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nytrazine strip, typically handled by forceps when inserted into the vagina, for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination.

There is need for a simple, rapidly carried out method which obviates problems associated with the conventional procedure; also, there is need for protection of vaginal tissue during pH detection, and there is auxiliary need for ease of excess moisture removal from the vagina, at the time of the pH test.

SUMMARY OF THE INVENTION

It is a major object of the invention to provide a significantly improved method which meets the above need, and overcomes prior problems, as referred to. Basically, the method of the invention includes the steps:

a) providing a pH detection means on a carrier stick, b) providing a protective porous layer adjacent said pH detection means, c) manipulating the stick to obtain pH detection of vaginal moisture, and including allowing vaginal moisture to penetrate said porous layer for contact with said pH detection means, d) and visually observing said detection means.

The protective porous layer provides a thin physical barrier between the pH detection means and vaginal tissue, as during a test, while at the same time allowing vaginal moisture to penetrate through the barrier to contact the pH detection means. The latter typically includes at least one of the following:

i) a pH measurement strip, as for example a Nytrazine strip, on the stick ii) a color comparison measurement means on the stick.

In addition an enlarged smooth surfaced protective tip may be provided at the end of the stick proximate the pH detection means and the protective barrier layer to facilitate comfortable insertion of that end of the stick, and those elements thereon, into the vagina.

Another object includes the steps:

a) providing a ph indication, color comparison measurement, and swabbing means on a carrier stick, b) manipulating the stick between its opposite ends to obtain pH indication of vaginal moisture at one end of the stick, c) visually interpreting that indication to also obtain pH measurement of such moisture near that one end of the stick, d) again manipulating the stick between its opposite ends, including endwise reversing it, to swab the vaginal cavity in the area from which pH indication was obtained, e) and disposing of the stick, whereby disposition of the pH indication, measurement and swabbing means is thereby obtained in one disposal step, f) said a) step including providing the pH indication means in the form of a strip on said one end of the stick, and g) providing a protective porous layer to extend adjacent at least one of the following:

$X_1$) said strip $X_2$) said color comparison measurement means.

As will appear, the a) step may include adhering a pH indication strip to one end of the stick and adhering a pH measurement colorimeter strip to the stick adjacent the pH indication strip, but between the indication strip and the swabbing means, leaving stick extent free for manual manipulation.

A smooth surfaced protective tip may be provided at the strip end of the stick, as referred to above, to facilitate comfortable insertion of that end of the stick in the vagina, and that tip may be provided in the form of a slotted sleeve fitted over or endwise adjacent the indicator strip.

It is another object to provide pH measurement means having color gradations in a series sequence, including locating the series lengthwise along the stick, adjacent the indication means. As will be seen, pH measurement means may be provided by winding it about one end of the stick.

A further object includes maintaining an elongated gap along the stick between the pH measurement means and the swabbing means, whereby the stick may be grasped at the gap for manipulation. In this regard, the swabbing means may be provided by attaching a moisture-absorbing swab to the other end of the stick, and in lengthwise spaced relation to both pH indicating means and pH measurement means.

Yet another object includes the provision of the pH measurement means to have a pH numerical sequence in a series associated with the color gradations, and including also locating the numerical sequence lengthwise along the stick.

Apparatus incorporating the invention includes, in combination a) an elongated stick, b) pH detecting means on the stick, at one end portion thereof, c) and a protective porous layer extending adjacent said pH detecting means.

As will appear, the protective porous layer may have a portion thereof attached or adhered to the stick, enabling it to be easily removed for enabling better visual observation of the pH detection means, after a test.

Yet another object includes provision of:

a) an elongated stick, b) pH indicating first means on the stick, at one end portion thereof, there being a protective porous barrier overlying said first means, c) color comparison pH measurement second means on the stick, spaced from that one end portion thereof, d) the stick projecting freely from the first and second means for manual manipulation to first obtain pH indication of vaginal moisture at one end of the stick, and to enable visual interpretation of that indication by color comparison with the second means, without manual release of the stick, e) the stick then being disposable to dispose of both first and second means in one disposal step.

The first means typically comprises a strip adhered to one end of the stick, with the second means then extending lengthwise along the stick, away from the first means; and the second means typically has color gradations in a series sequence lengthwise along the stick.

An additional object includes the provision in the referred apparatus of a swabbing means attached to the stick at the opposite end thereof, and in spaced relation to first and second means. In this regard, the swabbing means and second means typically have stick spacing therebetween of between 3 and 5 inches, enabling ready finger grasping of the stick and manipulation thereof, including rapid endwise reversal of the stick.

These and other objects and advantages of the invention, as well as the details of an illustrative embodiment, will be more fully understood from the following specification and drawings, in which:

DRAWING DESCRIPTION

FIG. 1 is a side elevational view of stick apparatus incorporating the invention;

FIG. 2 is an enlarged side view of one end portion of the FIG. 1 stick apparatus;

FIG. 3 is an enlarged section taken on lines 3—3 of FIG. 2;

FIG. 4 is an enlarged end view taken on lines 4—4 of FIG. 2;

FIG. 5 is an elevation, partly in section, showing a modification;

FIG. 6 is a side elevation of the FIG. 5 modification;

FIG. 7 is an end view taken on lines 7—7 of FIG. 6;

FIG. 8 is an elevation showing a further modification;

FIG. 9 is an elevation showing yet another modification;

FIG. 10 is a view like FIG. 2, showing a protective porous layer applied over a pH indicator strip;

FIG. 11 is a view like FIG. 10, but showing the protective layer also applied over the color comparison measurement means;

FIG. 12 is a view like FIG. 8, showing a protective porous layer applied over a pH indication strip; and FIG. 12a is a view like FIG. 12, but showing the protective porous layer extending over the color comparison measurement means.

DETAILED DESCRIPTION

In the drawings, an elongated, narrow carrier stick 10 may consist of wood, plastic, or other material. Provided on the carrier stick are:

a pH indication means, as generally shown at 11, at one end portion 10a of the stick;

a color comparison pH measurement means, as generally indicated at 12, spaced from stick end portion 10a, but close to 11; and a swabbing means, as generally indicated at 13 on the opposite end portion 10b of the stick.

As shown, the first means 11 may comprise a pH indication strip, such as a Nytrazine strip, wound about the stick end portion 10a and adhered to same as by an adhesive. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11;

and immediate visual readout of the pH number adjacent the selected band.

The stick projects freely at 10c away from the first and second means 11 and 12 for manual manipulation (see the grasping finger and thumb 18 and 19), to first obtain pH indication of vaginal moisture at one end of the stick, and to enable visual interpretation of that indication by color comparison with the second means, without manual release of the stick. The stick is then disposable, or may be disposed of, after a swabbing step to be described.

The swabbing means 13 may comprise a soft cotton swab, or other absorbent material, attached to the carrier stick at its opposite end, and in spaced relation to the first and second means 11 and 12. The lengthwise spacing "d" between 13 and 12 is such as to enable free manual manipulation of the stick; and such spacing is typically between 3 and 5 inches, enabling ready finger grasping of the stick and manipulation thereof, including rapid endwise reversal of the stick. In a specific example, "d" is about 4 inches, and the stick diameter is about ⅜ inch.

The method of measuring pH of vaginal moisture includes the steps:

a) providing a pH indication, color comparison measurement, and swabbing means on a carrier stick, b) manipulating the stick between its opposite ends to obtain pH indication of vaginal moisture at one end of the stick, c) visually interpreting that indication to also obtain pH measurement of such moisture near that one end of the stick, d) again manipulating the stick between its opposite ends, including endwise reversing it, to swab the vaginal cavity in the area from which pH indication was obtained, e) and disposing of the stick, whereby disposition of the pH indication, measurement and swabbing means is thereby obtained in one disposal step.

The overall sizes of 11, 12 and 13 are such as to enable ready insertion into the vagina, via stick manipulation at zone 10c, with ready stick reversal, as needed. Swabbing of the vagina 22 is typically carried at in conjunction with pH measurement, via stick manipulation and endwise reversal, to obtain best measurement results.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina, for pH measurement. The tip 20 may typically be formed integrally with a sleeve 20*a* assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal moisture or fluid may access the strip 11 via that opening. See for example elongated slot 22 in the sleeve wall 20*aa*. The sleeve and tip may consist of transparent, molded, plastic material, to facilitate viewing of a change of color of the strip 11.

In FIG. 8, the sleeve 20*a* is shortened and attached at sleeve end 20*a'* into flush, or near flush, relation with the surface of the strip, at a locus on stick end portion 10*a*. This leaves the remaining length 11*f* of the strip openly exposed for moisture contact.

In FIG. 9, the sleeve 20*a"* is also shortened and attached to the stick end portion 10*a*, and in endwise alignment with the strip 11. This also leaves the remaining length 11*f* of the strip openly exposed for moisture contact.

Referring now to the modification seen in FIG. 10, the elements the same as in FIG. 2 are given the same numerals. In addition a protective layer 40 in the form of a thin porous barrier, is applied adjacent the outer side of strip 11 so as to cover the latter (i.e. extend thereabout) and to be carried by the stick. Layer 40 allows vaginal moisture to penetrate through it and to contact the pH indicator strip 11, as during a test. Following the test, the strip 11 may be observed as described above, and for this purpose the layer 40 may be at least partly removed from adjacency to the strip, as by complete manual removal. Opposite end portions 40*a* and 40*b* of layer 40 may be initially attached as by light bonding or sticking to the ends of the strip 11, or to the stick, allowing pull-away removal of the layer at the end of the test. Such bonding agents are known, as on 3M Micropore Tape. Layer 40 acts as a barrier, during a test, to block direct contact of vaginal tissue with strip 11, preventing any possible irritation of such tissue. The end 10*d* of the stick may be free of the swabbing means 13.

In FIG. 11, the elongated layer 45 is like layer 40, but also extends over and about the color comparison measurement means 12, and is adhered, as described above, to the elements 11 and 12, as at 45*a* and 45*b* to completely cover 11 and 12 as during a test, while allowing pull-away of the layer 45 for visual observation of 11 and 12 after the test. Either one or both of 11 and 12 may be considered as a pH detecting means.

FIG. 12 is like FIG. 8, but layer 50 corresponding to layer 40 has its end 50*a* adhered to and about the sleeve 20*a'*, while end portion 50*b* is adhered to the right end of strip 11, as shown. Note smooth surfaced blunt knob 20, as referred to above.

FIG. 12*a* is like FIG. 12, except that the layer 60, corresponding to 50, is elongated to cover the color comparison measurement means 12, and to adhere at 60*b* to the rightward end of 12.

In FIGS. 10–13, the porous barriers, as at 40, 45, 50 and 60 may consist of one or more barrier tissue layers, as for example are used in incontinence pads. One example is the outer layer of the Kimberly Clark product NEW DEPEND. Another usable barrier is the 3M product known as MICROPORE tape. One side of such tape is "tacky", i.e. weakly adhesive, so that it will adhere along the tape length to the elements 11 and/or 12 referred to. Barriers 45 and 50 as referred to may comprise such tape material.

I claim:

1. In the method of measuring ph of vaginal moisture, the steps that include:

a) providing a ph indication, color comparison measurement, and swabbing means on a carrier stick, b) manipulating the stick between its opposite ends to obtain pH indication of vaginal moisture at one end of the stick, c) visually interpreting that indication to also obtain pH measurement of such moisture near that one end of the stick, d) again manipulating the stick between its opposite ends, including endwise reversing it, to swab the vaginal cavity in the area from which pH indication was obtained, e) and disposing of the stick, whereby disposition of the pH indication, measurement and swabbing means in the form of a strip on said one end of the stick, and f) said a) step including providing said pH indication means in the form of a strip on said one end of the stick, and g) providing a protective porous layer to extend along a portion of at least one of the following:

$X_1$) said strip $X_2$) said color comparison measurement means, h) and providing a smooth surfaced protective bulbous tip, said protective tip extending transversely of and in interfitting relation with the distal ends of said stick and of said porous layer endwise thereof, to be carried by said stick distal end.

2. The method of claim 1 including attaching a portion of said porous layer to said stick.

3. The method of claim 1 including locating said porous layer to extend completely about the said stick.

4. The method of claim 1 wherein said color comparison measurement means is provided to have color gradations in a series sequence, and including locating said series lengthwise along the stick.

5. The method of claim 4 wherein said pH measurement means also provided to have a pH numerical sequence in a series associated with said color gradations, and including also locating said numerical sequence lengthwise along the stick.

6. The method of claim 1 wherein said pH indication strip is provided by winding it about said one end of the stick, and adhering it thereto.

7. The method of claim 1 including maintaining a gap along the stick length between said pH indication means and said swabbing means, whereby the stick may be readily grasped at said gap for said manipulation.

8. The method of claim 6 including maintaining a gap along the stick length between said strip and sleeve, and said swabbing means, whereby the stick may be readily grasped at said gap for said manipulation without manual interference with any of said a) means.

9. The method of claim 1 wherein said swabbing means is provided by attaching a moisture-absorbing swab to the other end of said stick, and in spaced relation to both said pH indicating means and said pH measurement means.

10. The method of claim 7 wherein said gap is maintained to have a length between 3 and 5 inches.

11. The method of claim 7 wherein said gap is provided to have a length of about 4 inches.

12. The method of claim 1 wherein swabbing is effected both prior to and subsequent to the obtaining of pH indication, by endwise stick reversal, to facilitate rapid pH measurement.

13. In apparatus for measuring pH of vaginal moisture, the combination comprising:

a) and elongated carrier stick, b) pH indicating first means in the form of a strip on the stick, at one end portion thereof, c) color comparison pH measurement second means on the stick, spaced from said one end portion thereof, d) the stick projecting freely from said first and second means for manual manipulation to first obtain pH indication of vaginal moisture at said one end of the stick, and to enable visual interpretation of that indication by color comparison with said second means, without manual release of the stick, e) the stick then being disposable to dispose of both said first and second means in one disposal step, f) there being a protective porous layer extending along a portion of at least one of the following:
   $X_1$) said strip
   $X_2$) said color comparison measurement means, g) and including a smooth surfaced protective tip having bulb shape, said protective tip extending transversely of and in interfitting relation with the distal ends of said stick and of said porous layer endwise thereof, to be carried by said stick distal end.

14. The apparatus of claim 13 wherein said strip is adhered to said one end of the stick, and said second means extends lengthwise along the stick, away from said first means.

15. The apparatus of claim 13 wherein said porous layer has a portion thereof adhered to the stick.

16. The apparatus of claim 14 wherein said second means has color gradations in a series sequence lengthwise along the stick.

17. The apparatus of claim 14 wherein said first means comprises a Nytrazine strip.

18. The apparatus of claim 17 wherein said Nytrazine strip is wound about the stick at said one end thereof.

19. The apparatus of claim 13 including a vaginal moisture swabbing means attached to the stick at the opposite end thereof, and in spaced relation to said first and second means.

20. The apparatus of claim 19 wherein the swabbing means and second means have stick spacing therebetween of between 3 and 5 inches, enabling ready finger grasping of the stick and manipulation thereof, including rapid endwise reversal of the stick.

21. The apparatus of claim 20 wherein said spacing is about 4 inches.

22. The apparatus of claim 16 wherein there are pH numerical indications on the stick, in close association with said color gradations.

23. The apparatus of claim 13 wherein said porous layer terminates at a location characterized in that a substantial length of the strip remains freely and openly exposed outwardly.

24. The apparatus of claim 13 including a protective plastic sleeve extending about a portion of said stick in endwise alignment with said strip, said sleeve carrying said tip.

25. In apparatus to detect pH of vaginal moisture, the combination comprising
   a) an elongated stick,
   b) pH detecting means on the stick, at one end portion thereof,
   c) a protective porous layer extending along said pH detecting means,
   d) and including a smooth surfaced protective bulbous tip, said protective tip extending transversely of and in interfitting relation with the distal ends of said stick and of said porous layer endwise thereof, to be carried by said stick distal end.

26. The combination of claim 25 wherein said protective porous layer has a portion thereof attached to the stick.

27. The combination of claim 25 wherein said pH detecting means includes at least one of the following:
   i) a pH indicating strip
   ii) a color comparison measurement means.

28. In the method of detecting pH of vaginal moisture, the steps that include:
   a) providing a pH detection means on a carrier stick,
   b) providing a protective porous layer along said pH detection means, and providing a smooth surfaced protective tip having bulb shape, said protective tip extending transversely of and in interfitting relation with the distal ends of said stick and of said porous layer endwise thereof, to be carried by said stick distal end,
   c) manipulating the stick to obtain pH detection of vaginal moisture, and including allowing vaginal moisture to penetrate said porous layer for contact with said pH detection means,
   d) and visually observing said detection means.

29. The method of claim 28 including removing said porous layer from along said pH detection means to allow said visually observing of said detection means.

30. The method of claim 28 including providing said pH detection means to include at least one of the following:
   i) a pH indicating strip
   ii) a color comparison measurement means.

31. In the method of detecting pH of vaginal moisture, the steps that include:
   a) providing a pH detection means on a carrier stick,
   b) providing a protective porous layer, and locating said layer to extend about said pH detection means, on said stick, and providing a smooth surfaced protective tip having substantially bulb shape, said protective tip extending transversely of and in interfitting relation with the distal ends of said stick and of said porous layer endwise thereof, to be carried by said stick distal end,
   c) manipulating the stick to obtain pH detection of vaginal moisture, and including allowing vaginal moisture to penetrate said porous layer for contact with said pH detection means,
   d) and visually observing said detection means.

32. The method of claim 31 wherein said layer is provided in the form of a sleeve extending about the stick.

33. The method of claim 32 including removably attaching said sleeve to the stick.

34. The method of claim 33 including pulling the sleeve away from the stick to enable said visual observing.

35. The method of claim 32 wherein said pH detection means is provided in the form of a pH indicating strip, and including attaching said strip to the stick to extend at at least one side of the stick.

36. The method of claim 31 including providing a domed end on the stick, proximate said layer.

37. The method of claim 31 wherein said layer is provided in the form of a tissue layer extending adjacent said pH detection means.

38. The method of claim 37 wherein said pH detection means is provided in the form of a pH indicating strip, and including attaching said strip to the stick to extend at at least one side of the stick.

* * * * *